(12) United States Patent
Chen

(10) Patent No.: US 11,076,941 B2
(45) Date of Patent: Aug. 3, 2021

(54) DENTAL OPERATION-GUIDING STRUCTURE AND METHOD FOR PRODUCING THE SAME

(71) Applicant: Min-Chia Chen, New Taipei (TW)

(72) Inventor: Min-Chia Chen, New Taipei (TW)

( * ) Notice: Subject to any disclaimer, the term of this patent is extended or adjusted under 35 U.S.C. 154(b) by 265 days.

(21) Appl. No.: 15/951,046

(22) Filed: Apr. 11, 2018

(65) Prior Publication Data

US 2019/0314127 A1 Oct. 17, 2019

(51) Int. Cl.
*A61C 19/05* (2006.01)
*A61C 9/00* (2006.01)
*A61C 3/00* (2006.01)
*G06T 17/00* (2006.01)

(52) U.S. Cl.
CPC ............ *A61C 19/05* (2013.01); *A61C 9/0053* (2013.01); *A61C 3/00* (2013.01); *A61C 9/0006* (2013.01); *G06T 17/00* (2013.01)

(58) Field of Classification Search
CPC ..... A61C 19/05; A61C 9/0053; A61C 9/0006; A61C 3/00; G06T 17/00
See application file for complete search history.

(56) References Cited

U.S. PATENT DOCUMENTS

| | | | | |
|---|---|---|---|---|
| 5,133,660 A * | 7/1992 | Fenick | ..................... | A61B 6/14 433/173 |
| 7,108,511 B1 * | 9/2006 | Shatkin | .................. | A61C 1/084 433/174 |
| 8,465,291 B2 * | 6/2013 | Bell | ..................... | G09B 23/283 434/262 |
| 8,805,658 B2 * | 8/2014 | Pettersson | ............ | A61C 8/0096 703/6 |
| 2002/0031747 A1 * | 3/2002 | Laster | ..................... | A61C 1/084 433/173 |
| 2010/0124731 A1 * | 5/2010 | Groscurth | ................ | A61C 9/00 433/213 |
| 2011/0008751 A1 * | 1/2011 | Pettersson | .............. | A61C 1/084 433/167 |
| 2011/0045431 A1 * | 2/2011 | Groscurth | .............. | A61C 1/084 433/74 |
| 2013/0216974 A1 * | 8/2013 | Schmalzle | ............. | A61C 1/084 433/75 |

(Continued)

*Primary Examiner* — Nicholas D Lucchesi
*Assistant Examiner* — Hao D Mai

(57) ABSTRACT

A dental operation-guiding structure includes a bite plate, a marking plate, and at least one connection frame connecting the bite plate and the marking plate. The bite plate is occluded by lower and upper teeth of a human body. The marking plate includes a plate body and at least one window penetrating the plate body. The plate body is adjacent to a tissue surface, and the windows defines a position to be operated. By occluding the dental operation-guiding structure, practical positions, patterns and ranges for the operation can be easily defined. The method for producing the dental operation-guiding structure overlaps a 3D bone image of a target object onto a 3D teeth-mold image thereof to obtain a reconstructed 3D image including clear contours of bones and soft tissues, bases on the reconstructed 3D image to design the dental operation-guiding structure, and finally produces the dental operation-guiding structure by 3D printing.

3 Claims, 5 Drawing Sheets

(56) References Cited

U.S. PATENT DOCUMENTS

| | | | | |
|---|---|---|---|---|
| 2014/0057227 | A1* | 2/2014 | Cheng | A61C 8/009 433/173 |
| 2015/0238290 | A1* | 8/2015 | Wouters | G05B 15/02 700/98 |
| 2015/0272704 | A1* | 10/2015 | Watson | A61C 8/0009 433/76 |
| 2015/0327958 | A1* | 11/2015 | Llop | A61C 13/0004 433/213 |
| 2016/0278878 | A1* | 9/2016 | Watson | A61C 9/0046 |
| 2016/0346062 | A1* | 12/2016 | Lococo | A61C 19/04 |
| 2016/0374778 | A1* | 12/2016 | Grobbee | A61C 1/084 433/74 |
| 2017/0112592 | A1* | 4/2017 | Groscurth | A61B 6/032 |
| 2017/0165030 | A1* | 6/2017 | Liu | A61C 1/084 |
| 2018/0000553 | A1* | 1/2018 | Bratbak | A61B 17/3472 |
| 2019/0255778 | A1* | 8/2019 | Lucas | B29C 64/393 |
| 2019/0336245 | A1* | 11/2019 | Liacouras | A61C 1/084 |

\* cited by examiner

DENTAL OPERATION-GUIDING STRUCTURE AND METHOD FOR PRODUCING THE SAME

BACKGROUND OF INVENTION

1. Field of the Invention

The invention relates to a dental operation-guiding structure and a method for producing the same, and more particularly to the dental operation-guiding structure and the method for producing the same that can define a specific region for a corresponding dental operation through determination of patient's teeth occlusion and positioning.

2. Description of the Prior Art

Currently, the success in dental-related operations, such as, but not limited to, the lateral window sinus lifting or the piezoelectric alveolar decortication for orthodontic treatment, is almost relied on professional skills and experiences of the surgeon himself or herself to determine precisely a position, a pattern and a range for the operation. By having the lateral window sinus lifting as an example, which is usually performed prior to a dental implantation in a posterior area, an artificial tooth implantation can be processed after (1) forming a hole at the bone lamella aside to the maxillary sinus, (2) lifting the sinus mucosa upward, and (3) filling with a bone graft material so as to increase the thickness at the corresponding maxillary bone. On the other hand, the piezoelectric alveolar decortication for orthodontic treatment, usually applied within an orthodontic treatment, is: (1) to perform an alveolar bone removal upon the teeth under the orthodontic treatment, (2) to form fine cut slots extending in a vertical direction on the alveolar bone between the neighboring teeth, and (3) to apply high-frequency micro vibrations by a piezoelectric vibrator; such that remodeling ability of corresponding alveolar bone cells can be activated, teeth shifting can be accelerated, and time needed for the orthodontic treatment can be shortened.

Nevertheless, prior to a dental-related operation, a three-dimensional (3D, thereafter) image of a target object to be operated shall be prepared by the X-Ray photography or the computed tomography (CT, thereafter), for example, such that the dentist or surgeon can evaluate and confirm preferably a position, a pattern and a range for the operation. Since the X-Ray photography and the CT can only provide a clear 3D image for the bone, however, to those soft tissues covering the bone, such as the gum or the teeth muscle, no clear 3D images can be obtained. Further, even that hard tissues can be visible after the soft tissues are lifted at corresponding flaps, it is still possible that a precise position to be cut can't be easily located due to the existence of lateral flaps. Thus, in this circumstance, the surgeon can only depend on his/her own professional skills and experiences to estimate the correlation between the invisible bone under the visible soft tissue and the data obtained from the X-Ray photography or the computed tomography. Actually, the surgeon is hard to precisely determine the position, the pattern and the range for the operation simply by judging the appearance of the corresponding soft tissue. Further, while in the operation, the bleeding from cutting the soft tissue would somehow block the visibility of the operation area. All of these will definitely affect visional judgments of the surgeon, and bias the position, the pattern and the range for the operation. In addition, especially if the surgeon is green, the opportunity for a successful operation would be a long way to be achieved. Possible residua or hurts might be left behind to the human body having the operation. For example, while in performing a lateral window sinus lifting, biased or excessive holing would lead quite possibly to a sinus perforation, post-operational swelling and/or pains. Also, while in performing an alveolar orthopedic surgery, the tooth root might be hurt and cause the tooth to lose its activity or the like. Hence, a further improvement upon the art of preparing the dental-related operations is definitely necessary.

SUMMARY OF THE INVENTION

Accordingly, it is the primary object of the present invention to provide a dental operation-guiding structure for a patient to occlude and thus to define practically a position, a pattern and a range for the operation, such that the surgeon can operate precisely in accordance with the practical position, pattern and range. Thereupon, the dental operation can be performed easily and conveniently, the visibility problem caused by the bleeding can be substantially compensated, and also the occurrence of post-operational residua and/or hurts can be reduced to a minimum.

It is another object of the present invention to provide a method for producing a dental operation-guiding structure, that integrates a 3D CT bone image with another 3D teeth-mold image captured by a 3D oral-cavity scanner or a dental arch model so as to obtain an reconstructed 3D image showing clearly both the bone and the soft tissue. Further, based on the reconstructed 3D image, the dental operation-guiding structure to define practically a position, a pattern and a range for an accurate operation can be designed. Finally, the desired dental operation-guiding structure can be manufactured via 3D printing.

In the present invention, the dental operation-guiding structure, applied to a dental-related operation upon a human body, includes:

a bite plate, being to be occluded and thus positioned between lower and upper teeth of the human body;

a marking plate, including a plate body and at least one window penetrating the plate body: and at least one connection frame, connecting the bite plate and the marking plate:

wherein, when the bite plate is occluded and thus positioned between the lower and upper teeth, the plate body of the marking plate is located adjacent to a tissue surface of the human body, and the at least one window defines corresponding at least one area to be operated.

Preferably, the bite plate has an upper surface and a lower surface opposing to the upper surface, and each of the upper and lower surfaces has thereon a plurality of bite structures individually formed respective to corresponding patterns and positions of the lower and upper teeth.

Preferably, the dental operation-guiding structure is produced by 3D printing, and patterns and ranges of the at least one window define corresponding patterns and ranges of areas to be operated.

Preferably, while the dental operation-guiding structure is applied to a lateral window sinus lifting, the plate body of the marking plate is located adjacent to the tissue surface out of a maxillary sinus of the human body, and the at least one window, defines positions, patterns and ranges of holes to be cut on a bone lamella of the human body.

Preferably, while the dental operation-guiding structure is applied to an alveolar orthopedic surgery, the at least one window includes a plurality of slots extending approximately a vertical direction, and each of the plurality of slots defines a position, a pattern and a range of a cut to be cut on a cortical bone of the human body; wherein the plate body further has a plurality of through holes distributed among the plurality of slots.

The invention discloses a method for producing a dental operation-guiding structure, the dental operation-guiding structure being applied to a dental-related operation upon a human body, comprising the steps of:

Step (A): obtaining at least one 3D image of a target object of the human body that is scheduled to undergo the operation;

Step (B): reconstructing the at least one 3D image of the target object so as to obtain a reconstructed 3D image that can demonstrate contours of a bone and a soft tissue of the target object;

Step (C): basing on the reconstructed 3D image obtained in Step (B) to design a bite plate, a marking plate and at least one connection frame for the dental operation-guiding structure; wherein the bite plate is to be occluded and thus positioned between lower and upper teeth of the human body, the marking plate includes a plate body and at least one window penetrating the plate body, and the at least one connection frame connects the bite plate and the marking plate; wherein. when the bite plate is occluded and thus positioned between the lower and upper teeth, the plate body of the marking plate is located adjacent to a tissue surface of the human body, and the at least one window defines corresponding at least one area to be operated; and Step (D): applying a 3D printing method to produce the dental operation-guiding structure.

Preferably, the at least one 3D image of Step (A) includes a 3D bone image of the target object and a 3D teeth-mold image of the target object including the soft tissue; wherein the 3D bone image is provided by a CT scan, and the 3D teeth-mold image is obtained by one of the following means: (1) performing an internal scan in an oral cavity of the human body by a 3D oral-cavity scanner; and, (2) obtaining firstly a dental arch model of impression materials by a conventional teeth-impressing method, and then performing another 3D scan upon the dental arch model by a 3D scanner.

Preferably, Step (B) further includes the following steps:

Step (B1): determining a range of bone mineral density for the target object; and Step (B2): basing on the range of bone mineral density to reconstruct the at least one 3D image of the target object: wherein the reconstructed 3D image is obtained by overlapping the 3D teeth-mold image onto the 3D bone image by matching at least one tooth.

Preferably, in Step (C), the bite plate is designed in accordance with the 3D teeth-mold image, the marking plate is designed in accordance with the 3D bone image, and the at least one connection frame is designed in accordance with the bite plate and the marking plate and in a positive manner for improving operational visibility and operability.

All these objects are achieved by the dental operation-guiding structure and the method for producing the same described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

The invention disclosed herein is directed to a dental operation-guiding structure and a method for producing the same. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

The invention refers to a dental operation-guiding structure. which includes a bite plate, a marking plate, and at least one connection frame connecting the bite plate and the marking plate. The bite plate is occluded by lower and upper teeth of a human body. The marking plate includes a plate body and at least one window penetrating the plate body. The plate body is adjacent to a tissue surface, and the window defines a position to be operated. By occluding the dental operation-guiding structure, practical positions, patterns and ranges for the operation can be easily defined. The method for producing the dental operation-guiding structure overlaps a 3D bone image of a target object onto a 3D teeth-mold image thereof to obtain a reconstructed 3D image including clear contours of bones and soft tissues, bases on the reconstructed 3D image to design the dental operation-guiding structure. and finally produces the dental operation-guiding structure by 3D printing.

Figure 1:
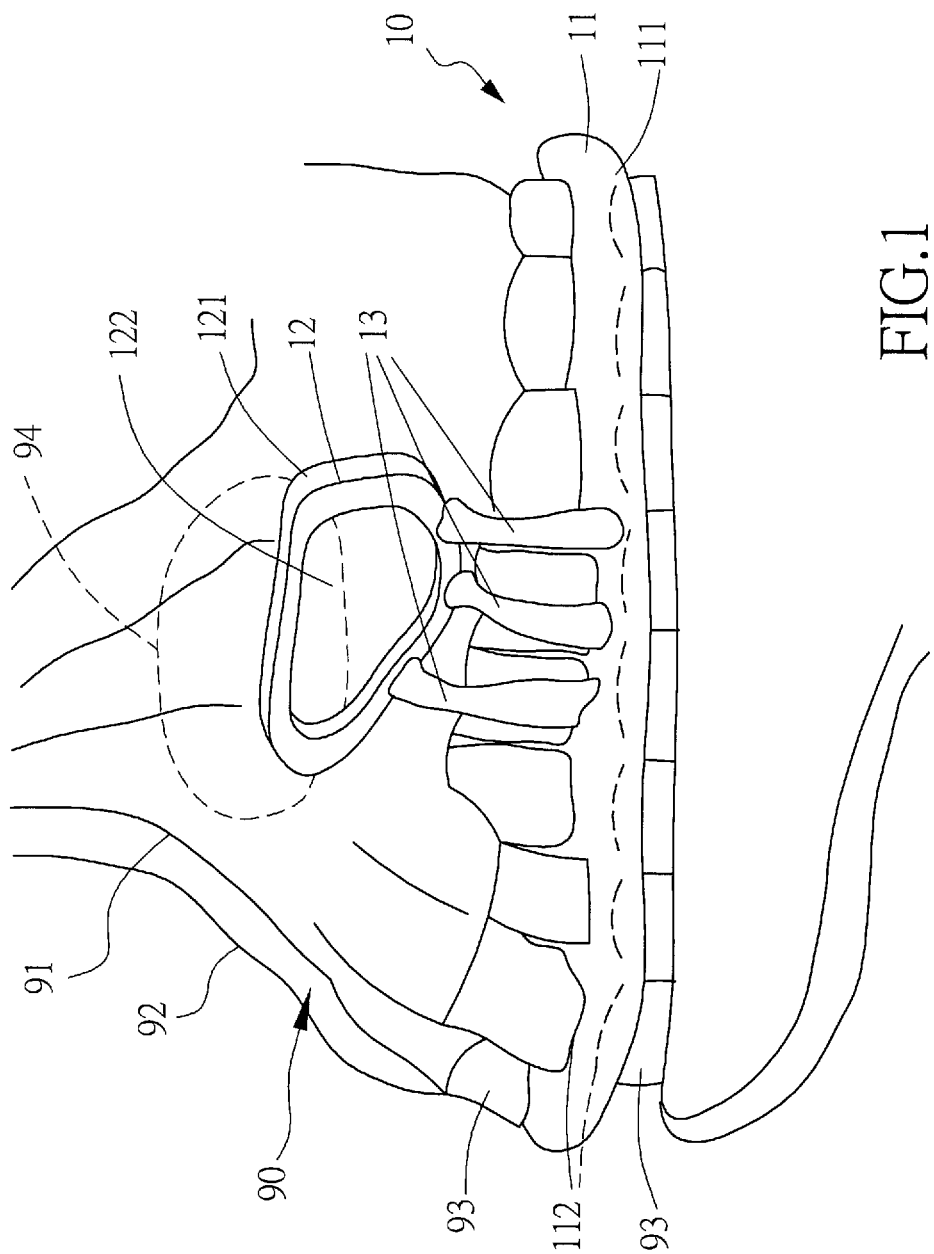
FIG. 1 demonstrates schematically that a first embodiment of the dental operation-guiding structure in accordance with the present invention is occluded in a human mouth.
Figure 2:
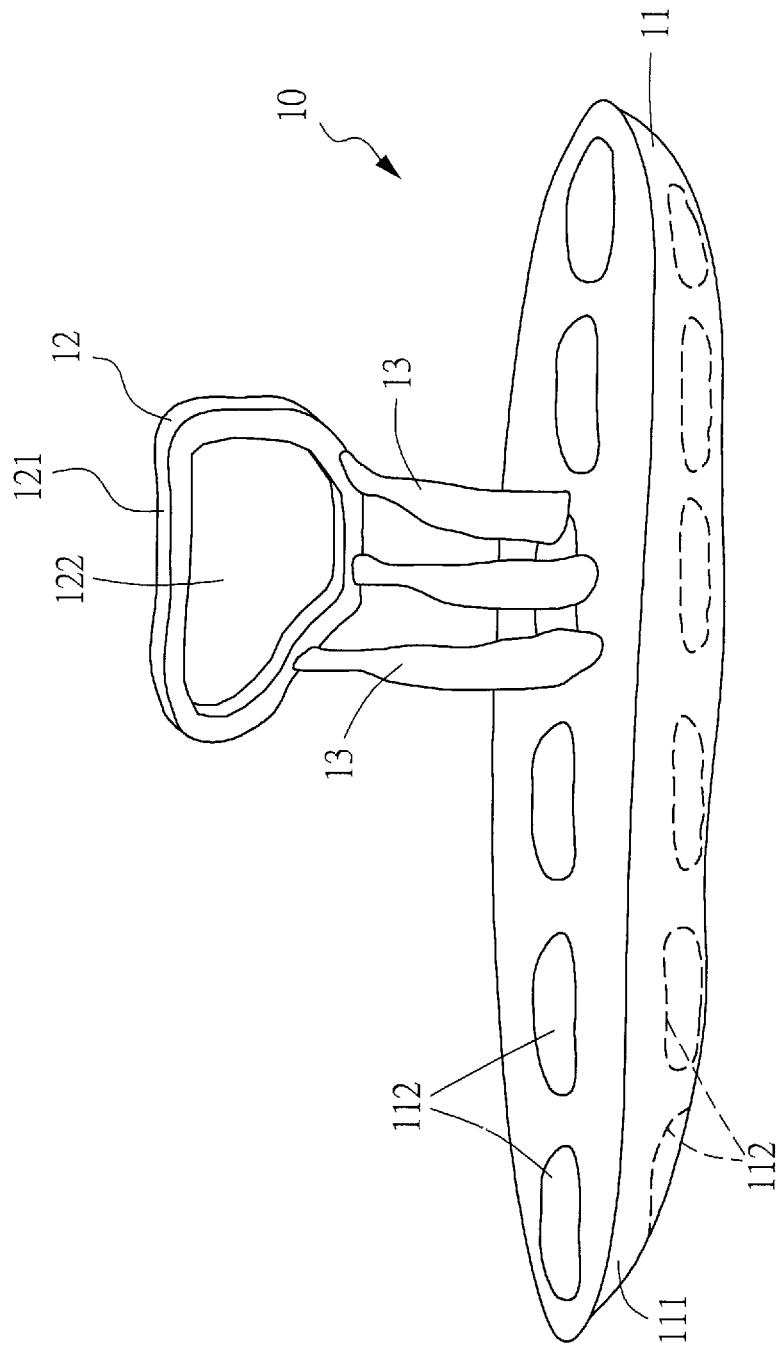
FIG. 2 is a schematic perspective view of the first embodiment of the dental operation-guiding structure of FIG. 1.

Refer now, to FIG. 1 and FIG. 2; where FIG. 1 demonstrates schematically that a first embodiment of the dental operation-guiding structure in accordance with the present invention is occluded in a human mouth (of a patient), and FIG. 2 is a schematic perspective view of the first embodiment of the dental operation-guiding structure of FIG. 1. The dental operation-guiding structure of the present invention is applicable for dental-related operations upon a human body, yet embodying of the present invention is not limited to that shown in FIG. 1 and FIG. 2. In fact, this first embodiment of the dental operation-guiding structure is particularly applied to an operation of lateral window sinus lifting.

In this first embodiment, the dental operation-guiding structure 10 includes a bite plate 11, a marking plate 12 and at least one connection frame 13. The bite plate 11 is to be occluded and thus positioned between the lower and upper teeth 93 of the human body. A mass 111 of the bite plate 11 has an upper surface and a lower surface opposing to the upper surface, and each of the upper and lower surfaces has thereon a plurality of bite structures 112. The plurality of bite structures 112 are individually formed respective to corresponding patterns and positions of the lower and upper teeth 93. The marking plate 12 includes a plate body 121 and at least one window 122 penetrating a thickness of the plate body 121. The at least one connection frame 13 is to connect, by bridging, the bite plate 11 and the marking plate 12 in a manner of the marking plate 12 being able to be held and supported, by the at least one connection frame 13, at a predetermined position above the bite plate 11. When the bite plate 11 is occluded and thus positioned between the lower and upper teeth 93 of the human body, the plate body 121 of the marking plate 12 is located right adjacent to a tissue surface 92 out of a maxillary sinus of the human body (i.e., the target object 90 to be operated). Also, the at least one window 122 is to define the position(s), pattern(s) and range(s) to be holed on a bone lamella 91 of the human body while in performing the lateral window sinus lifting. Thereupon, when the surgeon carries out the lateral window sinus lifting, he/she can base on the position(s), pattern(s) and range(s) of the windows) 122 on the marking plate 12 to make holes directly for entering the sinus cavity 94. Namely, there is no need anymore to have the knowledge of the position of the bone (bone lamella 91) covered by the soft tissue 92 of the human body. Thereby, the prior visibility problem caused by the bleeding would be substantially resolved, thus the operational accuracy can be enhanced, and also the risk of post-operational residua or hurts can be better avoided. In addition, according to the present invention, only upon the lower and upper teeth 93 to occlude the bite plate 11, the dental operation-guiding structure 10 and the marking plate 12 can be positioned precisely. No other positioning means is required anymore, such as (but not limited to) the gluing means, the screwing means, or the clamping means. In other words, when the dental operation-guiding structure 10 of the invention is used, the dental operation is performed during the lower and upper teeth 93 of patient being occluded.

Figure 3:
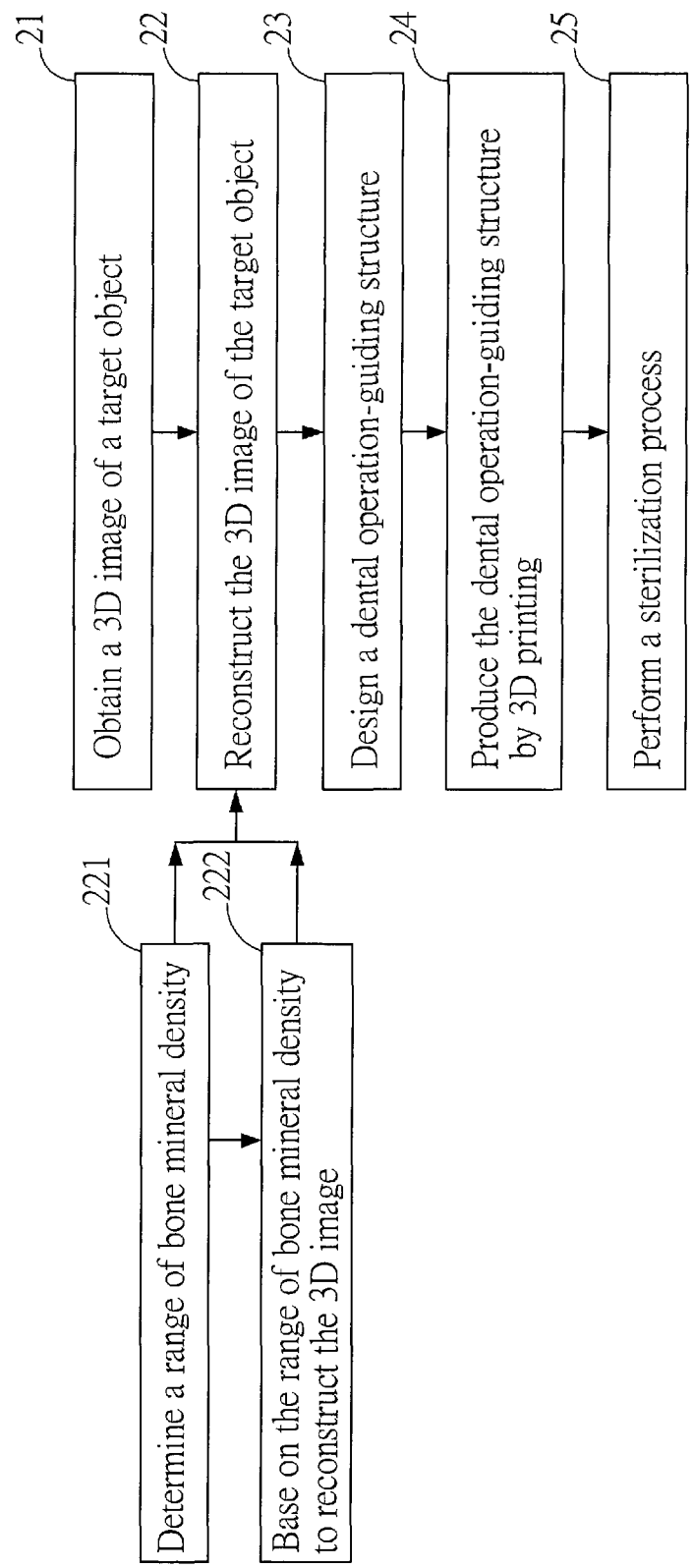
FIG. 3 is a flowchart of a preferred method for producing a dental operation-guiding structure in accordance with the present invention.

Referring now to FIG. 3, a flowchart of the preferred method for producing a dental operation-guiding structure in accordance with the present invention is shown. The dental operation-guiding structure is applicable to a dental-related operation upon a human body. The method includes the following steps.

Step 21: Obtain at least one 3D image of a target object of the human body that is scheduled to undergo the operation. In this embodiment, the at least one 3D image can include a 3D bone image of the target object, and a 3D teeth-mold image of the target object including soft tissues. The 3D bone image can be provided by a CT scan, and can be prepared as a digital data file that can be read and processed by a computer (such as, but not limited to, a digital data file with an ".STL" filename extension). The 3D teeth-mold image can be obtained by any of the following means: (1) performing an internal scan in an oral cavity of the human body by a 3D oral-cavity scanner: and, (2) obtaining firstly a dental arch model of impression materials by a conventional teeth-impressing, method, and then performing a 3D scan upon the dental arch model by a 3D scanner. Similarly, the 3D teeth-mold image can be prepared as a digital data file that can be read and processed by a computer (such as, but not limited to, a digital data file with an ".STL" filename extension). In this embodiment, any of the 3D teeth-mold image and the 3D bone image would include an image of a plurality of teeth nearby the target object.

Step 22: Reconstruct the at least one 3D image of the target object so as to obtain a reconstructed 3D image that can demonstrate contours of a bone and a teeth mold (including soft tissues) of the target object. In this embodiment, Step 22 can further include the following steps.

Step 221: Determine a range of bone mineral density for the target object: and

Step 222: Base on the range of bone mineral density to reconstruct the at least one 3D image of the target object.

It is understood that the bone mineral density (BMD), or called as a bone mass, varies from man to man, and different bone mineral densities would produce different CT images. For example, a typical bone mineral density would be in a range of 60-300 HU (Hounsfield unit) by being computed in accordance with the specifications of spiral CT scanners. For a bone with a lower BMD (60-200 HU), its sharpness of the CT image contours would be different to that for another bone with a higher BMD (201-300 HU). In particular, if a CBCT (Cone-beam CT) scanner for professional dentistry is used, the range of image density as well as the unit for measurement would be different. In a CBCT specification, an input image intensity is applied to judge the relative bone density. Generally, in the CBCT specification, the normal bone density is in a range of 300-2000, the lower bone density is below 300, and the higher bone density is above 2000. In this embodiment, 3D image-processing software, such as the Mimics Innovation Suite, can be introduced to determine a relevant range of bone mineral density or bone density for the target object, and then the 3D bone image can be obtained in accordance with the determined range of bone mineral density, such that the sharpness and accuracy of contours in the 3D bone image can be ensured.

In this embodiment, the reconstructed 3D image is obtained through 3D computer-aided design software, such as, but not limited to, the Mimics Innovation Suite. The 3D teeth-mold image is overlapped onto the 3D bone image by matching the at least one tooth. Thereupon, in this embodiment, the contour sharpness of the reconstructed 3D image of the target object would be contributed by both the 3D teeth-mold image (including soft tissues) and the 3D bone image (bone lamella). Thus, the aforesaid shortcomings of the prior art that judges the positions and ranges for operations simply by the 3D bone image can be improved significantly. In this embodiment, the reconstructed 3D image can be also prepared by a digital data file with an ".STL" filename extension.

Step 23: Base on the reconstructed 3D image obtained in Step 22 to design patterns and structures of a bite plate, a marking plate and at least one connection frame for the dental operation-guiding structure. In this step, the aforementioned 3D computer-aided design software can be introduced to design the dental operation-guiding structure. According to the contours of the teeth and teeth mold (including soft tissues) provided by the 3D teeth-mold image within the reconstructed 3D image, the position, the pattern and the range for the bite plate (including the bite structures) can be formulated. Also, according to the contours of the bone lamella provided by the 3D bone image within the reconstructed 3D image, the position, the pattern and the range for the marking plate (including the plate body and the windows) can be formulated. Further, based on the relative positioning and the contours of the bite plate and the marking plate, contours, the positions, the patterns and the ranges for the at least one connection frame that connects the marking plate and the bite plate can be formulated in a positive manner for improving operational visibility and operability. As the aforesaid design of the dental operation-guiding structure is completed, corresponding 3D design plots of the dental operation-guiding structure can be outputted and stored, preferably in, but not limited to, a format of the data file with an ".STL" filename extension. In addition, these 3D design plots of the dental operation-guiding structure can be overlapped back to the 3D bone image and/or the 3D teeth-mold image, such that the operational positions, patterns and ranges defined by the dental operation-guiding structure can be examined and confirmed. Since the bite plate is designed to be occluded by corresponding teeth, thus the design thereof shall take the gums and neighboring tissues into consideration. Thus, the strategy of designing the position, the pattern and the range of the bite plate by utilizing the contours the teeth and the teeth mold (including the soft tissues) within the 3D teeth-mold image can improve the design accuracy of the bite plate. On the other hand, since the marking plate is applied to define the positions, the patterns and the ranges of the operation, so the strategy of designing the marking plate (including the plate body and the windows) by utilizing the contours of the bone lamella within the 3D bone image can enhance the design accuracy of the marking plate.

Step 24: Apply a 3D printing method to produce the dental operation-guiding structure. After the design of the dental operation-guiding structure is finished, the digital data file(s) of the dental operation-guiding structure can be inputted or uploaded to a 3D printing machine, such that a real dental operation-guiding structure can be produced by 3D printing. In this embodiment, the dental operation-guiding structure can be made of a photocurable resin material of the medical-grade epoxy resins. The 3D printing machine can use the photocurable resin material in a colloidal or liquid form to print out the dental operation-guiding structure. At the same time, a light with a specific wavelength range (for example, but not limited to, an ultraviolet light) can be introduced by radiation to cure the printed material. Thereupon, a product of the dental operation-guiding structure that complies with the 3D design plots thereof can be obtained.

Step 25: Apply a sterilization process. The out-printed dental operation-guiding structure is then sterilized and further prepared by following treatments so as to be ready for usage in operations.

Figure 4:
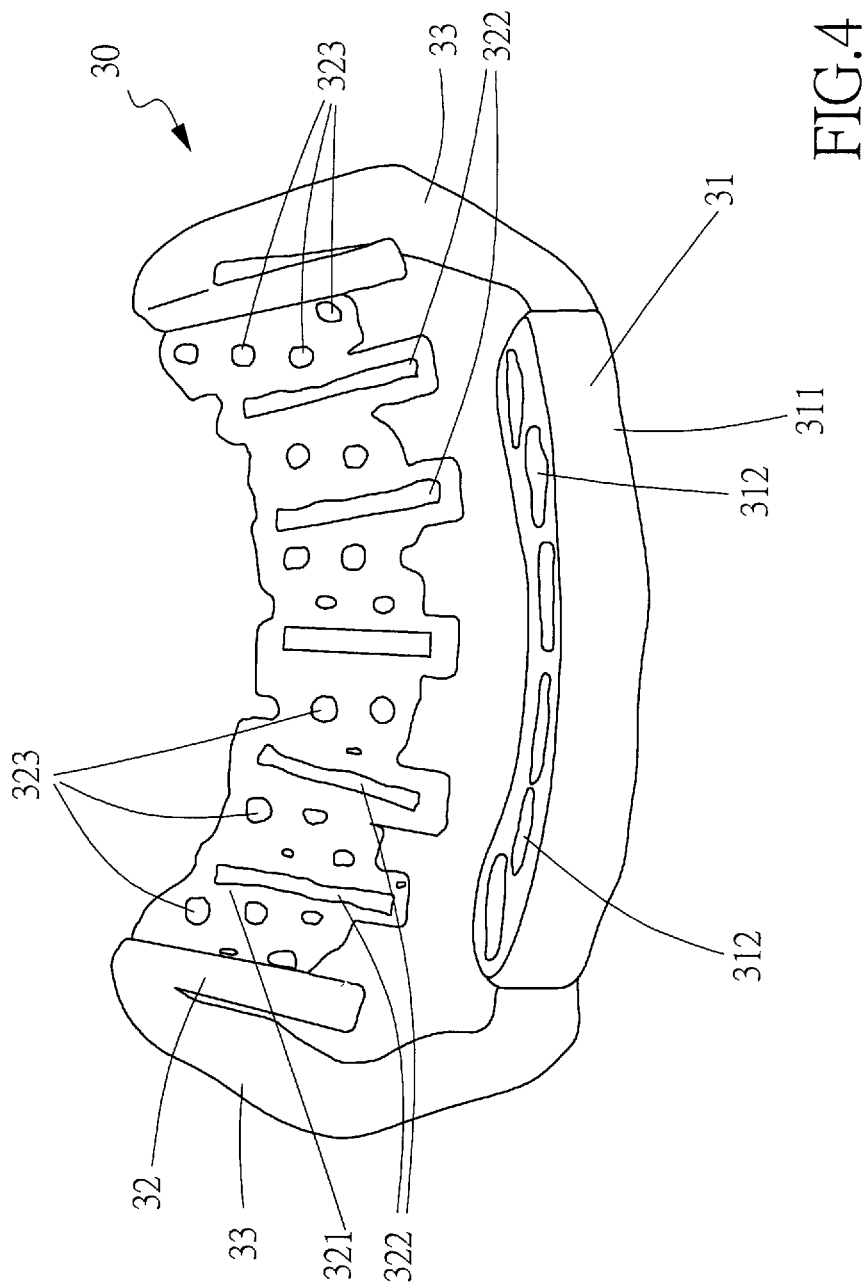
FIG. 4 is a schematic perspective view of a second embodiment of the dental operation-guiding structure in accordance with the present invention.
Figure 5:
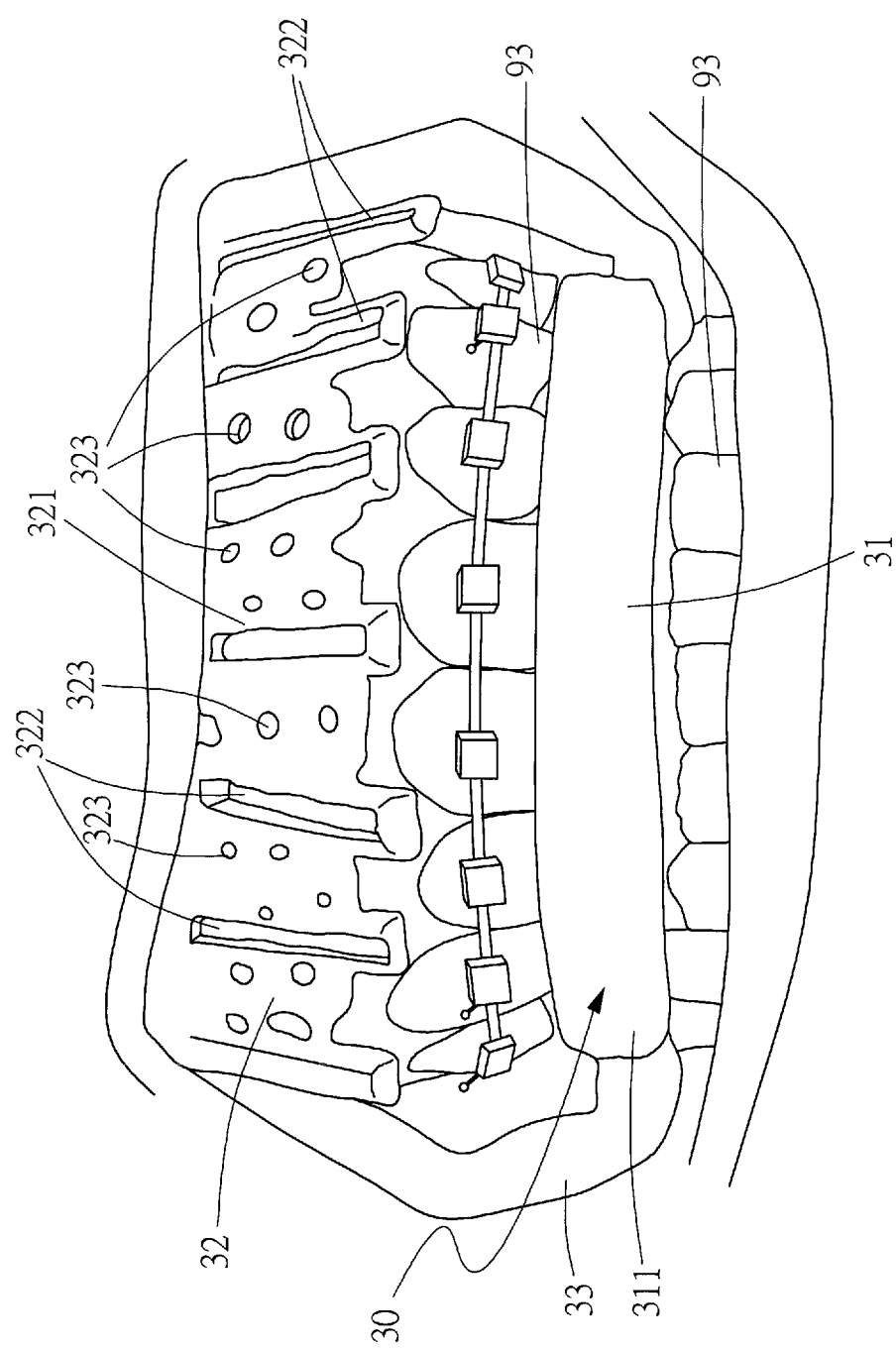
FIG. 5 demonstrates schematically that the second embodiment of the dental operation-guiding structure of FIG. 4 is occluded in a human mouth.

Refer now to FIG. 4 and FIG. 5; where FIG. 4 is a schematic perspective view of a second embodiment of the dental operation-guiding structure in accordance with the present invention, and FIG. 5 demonstrates schematically that the second embodiment of the dental operation-guiding structure of FIG. 4 is occluded in a human mouth. In this second embodiment, the dental operation-guiding structure is applicable to a piezoelectric alveolar decortication for orthodontic treatment.

In the second embodiment, the dental operation-guiding structure 30 includes a bite plate 31, a marking plate 32 and at least one connection frame 33. The bite plate 31 is to be occluded and thus positioned between the lower and upper teeth 93 of the human body. A mass 311 of the bite plate 31 has an upper surface and a lower surface opposing to the upper surface, and each of the upper and lower surfaces has thereon a plurality of bite structures 312. The plurality of bite structures 312 are individually formed respective to corresponding patterns and positions of the lower and upper teeth 93. The marking plate 32 includes a plate body 321 and at least one window, 322 penetrating a thickness of the plate body 321. The at least one connection frame 33 is to connect, by bridging, the bite plate 31 and the marking, plate 32 in a manner of the marking plate 32 being able to be held and supported, by the at least one connection frame 13, at a predetermined position above the bite plate 31. In this second embodiment, the at least one window 322 is formulated by a plurality of slots extending approximately in a vertical direction. The position, the pattern and the range of each the slot define respectively the position, the pattern and the range of the cortical bone to be cut in the alveolar orthopedic surgery. In addition, the plate body 321 further has thereon a plurality of through holes 323 distributed between two neighboring ones of the slots 322. When the bite plate 31 is occluded and thus positioned between the lower and upper teeth 93 of the human body, the plate body 321 of the marking plate 32 is located adjacent to a surface of the gum tissue of the human body, and, at this time, the positions, the patterns and the ranges of the at least one window 322 are those for performing the cutting on the cortical hone and the high-speed micro vibrations (by a piezoelectric vibrator) during the alveolar orthopedic surgery. In determining the patterns and the positions of the at least one connection frame 33, the dental braces on the lower and upper teeth 93 shall be detoured, and the connection frame 33 shall not block the visible range of the surgeon while in performing the cutting of the cortical bone and the high-speed micro vibrations via the piezoelectric vibrators. Through these slots (i.e., the windows 322), the surgeon can precisely perform the cutting of the cortical bone and the high-speed micro vibrations via the piezoelectric vibrators right at the correct positions, the correct patterns and the correct ranges, without hurting the neighboring tooth roots. Also, since a substantial amount of heat would be generated from operating the piezoelectric vibrators, thus a water flow for a cooling purpose is usually introduced to cool down the operation areas under the micro vibrations. In the present invention, these through holes 323 between the neighboring slots (windows 322) can be used to flow the cooling water through the marking plate 32, so that the heat-dissipation performance can be enhanced. Thereupon, while a surgeon perform the piezoelectric alveolar decortication for orthodontic treatment, he/she can base on the positions, the patterns and the ranges of the windows 322 (slots) on the marking plate 32 to perform the cutting upon the cortical bone and to apply the high-speed micro vibrations. Thus, no more guess upon the positions of the bone and the tooth roots covered by the soft tissues of the human body is needed. Also, the visibility problem caused by the bleeding can be substantially to waived, the operational accuracy cam be improved, and the occurrence of post-operational residua and/or hurts can be reduced to a minimum.

While the present invention has been particularly shown and described with reference to a preferred embodiment, it will be understood by those skilled in the art that various changes in form and detail may be without departing from the spirit and scope of the present invention.

What is claimed is:

1. A dental operation-guiding structure, applied to a dental-related operation upon a human body, comprising:
    a bite plate, capable of being adapted to be occluded and thus positioned between lower and upper teeth of the human body;
    a marking plate, including a plate body and at least one window penetrating the plate body; and
    at least one connection frame, connecting the bite plate and the marking plate;
    wherein, when the bite plate is adapted to be occluded and thus positioned between the lower and upper teeth, the plate body of the marking plate is configured for placement adjacent to a tissue surface of the human body, and the at least one window defines corresponding at least one area to be operated;
    wherein, the plate body further has a plurality of through holes distributed near to the at least one window; said through holes are used to flow a cooling water therethrough in order to improve a heat-dissipation performance of the dental operation-guiding structure during the dental-related operation;

wherein the bite plate has an upper surface and a lower surface opposing to the upper surface, and each of the upper and lower surfaces has thereon a plurality of bite structures individually formed respective to corresponding patterns and positions of the lower and upper teeth;

wherein, while the dental operation-guiding structure is applied to an alveolar orthopedic surgery, the at least one window includes a plurality of slots extending approximately a vertical direction, and each of the plurality of slots defines a position, a pattern and a range of a cut configured for cutting on a cortical bone of the human body; wherein the through holes are distributed among the plurality of slots for allowing said cooling water to flow through the through holes in order to improve the heat-dissipation performance of the dental operation-guiding structure during the alveolar orthopedic surgery;

wherein, the alveolar orthopedic surgery is operated by using a piezoelectric vibrator; the bite plate is adapted to be occluded by the lower and upper teeth of the human body, such that the upper and lower teeth are in an occluded state during the alveolar orthopedic surgery; all of the slots and the through holes are adapted to be exposed on a front surface of a gum tissue of the human body, in addition, there is at least one said through hole being located between any two neighboring said slots.

2. The dental operation-guiding structure of claim 1, wherein the dental operation-guiding structure is produced by 3D printing, and patterns and ranges of the at least one window define corresponding patterns and ranges of areas to be operated.

3. The dental operation-guiding structure of claim 1, wherein, at least one dental brace is capable of being adapted to be mounted on at least one of the lower and upper teeth; and the at least one connection frame detours around the at least one dental brace.

* * * * *